(12) United States Patent
Tian et al.

(10) Patent No.: US 11,883,627 B2
(45) Date of Patent: Jan. 30, 2024

(54) DRIVING STRUCTURE AND INJECTION MACHINE

(71) Applicant: SHENZHEN ZPW TECHNOLOGY CO., LTD., Guangdong (CN)

(72) Inventors: Yue Tian, Guangdong (CN); Shaodong Ren, Guangdong (CN)

(73) Assignee: SHENZHEN ZPW TECHNOLOGY CO., LTD., Guangdong (CN)

( * ) Notice: Subject to any disclaimer, the term of this patent is extended or adjusted under 35 U.S.C. 154(b) by 652 days.

(21) Appl. No.: 17/252,970

(22) PCT Filed: Mar. 27, 2020

(86) PCT No.: PCT/CN2020/081686
§ 371 (c)(1),
(2) Date: Dec. 16, 2020

(87) PCT Pub. No.: WO2020/200094
PCT Pub. Date: Oct. 8, 2020

(65) Prior Publication Data
US 2021/0128826 A1      May 6, 2021

(30) Foreign Application Priority Data

Apr. 3, 2019 (CN) .......................... 201910264348.4
Nov. 14, 2019 (CN) .......................... 201911111498.8
Nov. 14, 2019 (CN) .......................... 201911111510.5

(51) Int. Cl.
*A61M 5/145* (2006.01)
*A61M 5/142* (2006.01)

(52) U.S. Cl.
CPC .............................. *A61M 5/14248* (2013.01)

(58) Field of Classification Search
CPC ........ A61D 1/025; A61M 2005/14252; A61M 5/16827; A61M 2005/14506; A61M 2005/14533; A61M 5/142
See application file for complete search history.

(56) References Cited

U.S. PATENT DOCUMENTS 6,264,637 B1     7/2001 Hogan

FOREIGN PATENT DOCUMENTS

| CN | 102582098 A | 7/2012 |
|---|---|---|
| CN | 102846407 A | 1/2013 |

(Continued)

OTHER PUBLICATIONS

International Search Report and Written Opinion for corresponding International Application No. PCT/CN2020/081686 dated May 27, 2020.

*Primary Examiner* — Deanna K Hall
(74) *Attorney, Agent, or Firm* — Renner, Otto, Boisselle & Sklar, LLP

(57) ABSTRACT

A driving structure and an injection machine are disclosed. The driving structure includes: a driving device, a first swinging assembly and a second swinging assembly, the first swinging assembly and the second swinging assembly both comprise a swinging block and a moving block, the swinging block is in contact with the moving block, the swinging block of the first swinging assembly and the swinging block of the second swinging assembly are both connected with an output end of the driving device, the swinging block in the same swinging assembly is configured to drive the moving block to move, and a working stroke of the moving block in the first swinging assembly and a working stroke of the moving block in the second swinging assembly are carried out at intervals.

20 Claims, 10 Drawing Sheets

(56) References Cited

FOREIGN PATENT DOCUMENTS

| | | |
|---|---|---|
| CN | 203915139 U | 11/2014 |
| CN | 106983579 A | 7/2017 |
| CN | 107412903 A | 12/2017 |

DRIVING STRUCTURE AND INJECTION MACHINE

This application is a national phase of International Application No. PCT/CN2020/081686, filed Mar. 27, 2020.

TECHNICAL FIELD

The present invention relates to the field of injection machine technologies, and more particularly, to a driving structure and an injection machine.

BACKGROUND

A driving structure is a commonly used technical means in the existing technology, but in actual production, most of the working modes are driving a set of structures to move through one driving structure. However, this mode may occupy a large number of driving structures, so that a whole weight of a produced device is heavier, thereby affecting the working performance of the device.

SUMMARY

The present invention is intended to address at least one of the technical problems in the existing technology. For this purpose, the present invention provides a driving structure and an injection machine capable of reducing a weight of the driving structure.

The present invention provides a driving structure for driving an injection device to inject liquid, which includes: a driving device, a first swinging assembly and a second swinging assembly, wherein the first swinging assembly and the second swinging assembly both comprise a swinging block and a moving block, the swinging block is in contact with the moving block, the swinging block of the first swinging assembly and the swinging block of the second swinging assembly are both connected with an output end of the driving device, the swinging block in the same swinging assembly drives the moving block to move, and a working stroke of the moving block in the first swinging assembly and a working stroke of the moving block in the second swinging assembly are carried out at intervals; further includes a first track and a second track, wherein the swinging block of the first swinging assembly comprises a first swinging block, the moving block of the first swinging assembly comprises a first moving block, the swinging block of the second swinging assembly comprises a second swinging block, the moving block of the second swinging assembly comprises a second moving block, the first moving block is capable of moving along the first track, and the second moving block is capable of moving along the second track.

As a further improvement of the above technical solution, the driving device includes a first output end and a second output end, the swinging block of the first swinging assembly is connected with the first output end of the driving device, and the swinging block of the second swinging assembly is connected with the second output end of the driving device.

As a further improvement of the above technical solution, the swinging block includes a fixed end and a movable end, the fixed end is connected with the output end, the swinging block is capable of moving around the fixed end, and the movable end is used for driving the moving block to move.

As a further improvement of the above technical solution, the fixed end is provided with a roller, the moving block is provided with a through hole, the swinging block is located in the through hole, and the swinging block is connected with an inner wall of the through hole through the roller for driving the moving block to move.

As a further improvement of the above technical solution, the driving structure further includes a first track and a second track, wherein the first swinging assembly includes a first swinging block and a first moving block, the second swinging assembly includes a second swinging block and a second moving block, the first track penetrates through the first moving block, the first moving block is capable of moving along the first track, the second track penetrates through the second moving block, and the second moving block is capable of moving along the second track.

As a further improvement of the above technical solution, an angle difference between the swinging block of the second swinging assembly and the swinging block of the first swinging assembly ranges from 80° to 180°.

As a further improvement of the above technical solution, the first swinging assembly and the second swinging assembly both have a crank-slider structure, the swinging block is a crank mechanism, and the moving block is a slider structure.

As a further improvement of the above technical solution, a length of the through hole in an X-axis direction is greater than or equal to a distance between the fixed end and the movable end and less than or equal to twice the distance between the fixed end and the movable end, and a length of the through hole in a Y-axis direction is greater than or equal to twice the distance between the fixed end and the movable end.

The present invention further provides an injection machine, which includes an injection device, a liquid storage tank and the driving structure, wherein an outlet of the liquid storage tank is communicated with an inlet of the injection device, and the liquid storage tank is used for conveying liquid into the injection device.

As a further improvement of the above technical solution, the injection machine further includes a pushing block and an infusion tube, wherein one end of the infusion tube is connected with the liquid storage tank, the other end of the outlet of the infusion tube is connected with the inlet of the injection device, the pushing block is provided with a limiting groove, at least a part of the infusion tube is located in the limiting groove, the pushing block is connected with the second moving block, and the second moving block drives the pushing block to move to drive the injection device to complete the penetrating action.

As a further improvement of the above technical solution, the working stroke of the second moving block occurs before the working stroke of the first moving block.

As a further improvement of the above technical solution, the injection machine further includes a clamping block, wherein the clamping block is arranged adjacent to the liquid storage tank, the clamping block is also provided with a bayonet, and the bayonet limits the infusion tube.

As a further improvement of the above technical solution, the injection machine further includes a wearing structure, wherein the injection device is connected with the wearing structure and moves relative to the wearing device, and the wearing structure is used for being connected with limbs of a user.

As a further improvement of the above technical solution, the injection machine further includes an outer tube, wherein the injection device is capable of moving in the outer tube, the outer tube includes a needle outlet, the needle outlet is arranged adjacent to the wearing structure, and the injection device is capable of extending outwardly from the needle outlet.

As a further improvement of the above technical solution, at least a part of the injection device is capable of being retracted into the outer tube.

As a further improvement of the above technical solution, the wearing structure includes a sleeve structure for being sheathed with limbs, and the sleeve structure is capable of being deformed to adjust a diameter.

As a further improvement of the above technical solution, the sleeve structure includes a base and a wearing device, at least two clamping grooves are arranged on the wearing device in a length direction, a hook is arranged on the base, one end of the wearing device is connected with the base, and the other end of the wearing device is clamped on the hook through the clamping grooves;

or, the sleeve structure includes a base and a wearing device, at least two clamping grooves are arranged on the wearing device in a length direction, two hooks are arranged on the base, one end of the wearing device is clamped on one hook through one clamping groove, and the other end of the wearing device is clamped on the other hook through the other clamping groove.

As a further improvement of the above technical solution, the sleeve structure is made of an elastic material, and a cross section of the sleeve structure is in a "C" shape.

As a further improvement of the above technical solution, the injection machine further includes a limiting device, wherein the injection device includes a needle, the limiting device includes a baffle, and the baffle is located on a side of the sleeve structure close to the needle and located on a path where the limbs extend out.

As a further improvement of the above technical solution, the injection machine further includes a triggering device, wherein the triggering device is connected with the wearing structure, the triggering device is electrically connected with the driving device, and an output end of the driving device is connected with the injection device;

or, the injection machine further includes a triggering device and the driving device, the triggering device is connected with the injection device, the triggering device is electrically connected with the driving device, and an output end of the driving device is connected with the injection device.

As a further improvement of the above technical solution, the injection machine includes a triggering device, a first wearing structure, a second wearing structure, a first injection device and a second injection device, wherein the first injection device is connected with the first wearing structure, the second injection device is connected with the second wearing structure, the first wearing structure is connected with the second wearing structure, and at least one injection device is connected with the triggering device.

As a further improvement of the above technical solution, the injection machine further includes a driving member and the injection device, wherein one end of the driving member is connected with the second moving block, the other end of the driving member is connected with an injector, and the injector is pushed through the second moving block to complete the penetrating action of the injector relative to an object;

or, the injection machine further includes a frame body, a driving member and an elastic structure, one end of the driving member is connected with the second moving block, the other end of the driving member is connected with an injector, one end of the elastic structure is connected with the frame body, the other end of the elastic structure is abutted against the injector, when the driving member pulls the injection device, the elastic structure is compressed or stretched, and a force of restoring deformation of the elastic structure is used for completing the penetrating action of the injector relative to an object.

As a further improvement of the above technical solution, the injection machine further includes an infusion tube and a working portion, wherein the injector is located in the working portion, one end of the infusion tube is connected with the liquid storage tank, and the other end of the infusion tube is connected with the injector.

As a further improvement of the above technical solution, the working portion includes an arc-shaped contact surface, the arc-shaped contact surface is used for being in contact with the object, the arc-shaped contact surface is provided with an outlet hole, and the needle of the injection device of the injector is capable of extending out of the outlet hole to the working portion.

As a further improvement of the above technical solution, the injection machine further includes the working portion which includes a first bracket and a second bracket, wherein the first bracket includes a first inclined plane, the second bracket includes a second inclined plane, the first bracket and the second bracket are arranged adjacently, and the first inclined plane and the second inclined plane form a V-shaped structure for supporting the object;

or, the injection machine further includes the working portion which includes a first bracket and a second bracket, the first bracket includes a first inclined plane, the second bracket includes a second inclined plane, the first bracket and the second bracket are arranged adjacently, the first inclined plane and the second inclined plane form a V-shaped structure for supporting the object, and the first bracket and the second bracket rotate relatively, thus adjusting an angle between the first inclined plane and the second inclined plane and adjusting a size of the V-shaped structure.

As a further improvement of the above technical solution, the injection machine further includes a first bracket, a second bracket and a compression bar, wherein the first bracket and the second bracket are respectively located at one end of the compression bar, the first bracket includes a first inclined plane, the second bracket includes a second inclined plane, the compression bar includes an arc plane, the first inclined plane, the arc plane and the second inclined plane form the arc-shaped contact surface, and the arc-shaped contact surface is used for being in contact with the object.

As a further improvement of the above technical solution, the first bracket and the second bracket rotate relative to the compression bar, the first bracket and the second bracket are respectively located at one end of the compression bar, the first bracket includes the first inclined plane, the second bracket includes the second inclined plane, the compression bar includes the arc plane, and when the first bracket and the second bracket are located on positions far away from the compression bar, the first inclined plane, the second inclined plane and the arc plane form the arc-shaped contact surface.

As a further improvement of the above technical solution, the working portion is provided with a triggering device.

As a further improvement of the above technical solution, the injection machine further includes a triggering device, a connecting block and a connecting rod, wherein one end of the connecting block is connected with an output end of the driving device, the other end of the connecting block is rotatably connected with the connecting rod, an end of the connecting rod far away from the connecting block is connected with the injection device, the triggering device is located on a side of the connecting block close to the compression bar, and when the driving member drives the compression bar to move, the triggering device is capable of being triggered; and the triggering device is located on the first inclined plane, the second inclined plane or the arc plane.

As a further improvement of the above technical solution, the injection machine further includes a piston, wherein the injection device is connected with the first moving block, and the first moving block drives the piston to move relative to the liquid storage tank, thus driving the liquid storage tank to complete an action of conveying the liquid in the liquid storage tank to the injection device;

or, the outlet of the liquid storage tank is communicated with the inlet of the injection device, the injection device is connected with the second moving block, a tank body of the liquid storage tank is capable of being extended and retracted to change a volume of the liquid storage tank, the tank body of the liquid storage tank is connected with the first moving block of the driving structure, and the volume of the liquid storage tank is changed by driving of the driving structure.

As a further improvement of the above technical solution, the liquid storage tank is provided with a feed inlet for supplementing the liquid into the liquid storage tank, and an end far away from the needle of the injection device is communicated with the outside for supplementing the liquid into the liquid storage tank;

or the liquid storage tank is detachably connected with the injection device.

As a further improvement of the above technical solution, the injection machine further includes a limiting block, wherein the limiting block is used for limiting the piston, so that a side of the piston outside the liquid storage tank is limited by the limiting block during moving, thus limiting a stroke of the piston, and adjusting a volume of liquid injected through the piston to the needle.

As a further improvement of the above technical solution, the injection machine further includes a first injector, a second injector, a first connecting rod, a second connecting rod and a connecting block, wherein one end of the connecting block is connected with the driving member, the other end of the connecting block is connected with the first connecting rod and the second connecting rod, one end of the first connecting rod is rotatably connected with the connecting block, the other end of the first connecting rod is rotatably connected with the first injector, one end of the second connecting rod is rotatably connected with the connecting block, and the other end of the second connecting rod is rotatably connected with the first injector; and the working portion includes a frame body, a first bracket and a second bracket, the first injector is connected with the first bracket, the first bracket is provided with a first outlet hole, the needle of the first injector is capable of extending out of the working portion relative to the first outlet hole, the second bracket is provided with a second outlet hole, and the needle of the second injector is capable of extending out of the working portion relative to the second outlet hole.

Beneficial effect: since the first swinging assembly and the second swinging assembly can be simultaneously driven to move by the same driving structure, a number of the driving devices is reduced and a weight of the driving structure is reduced in a process of completing the device of the driving structure.

Figure 1:
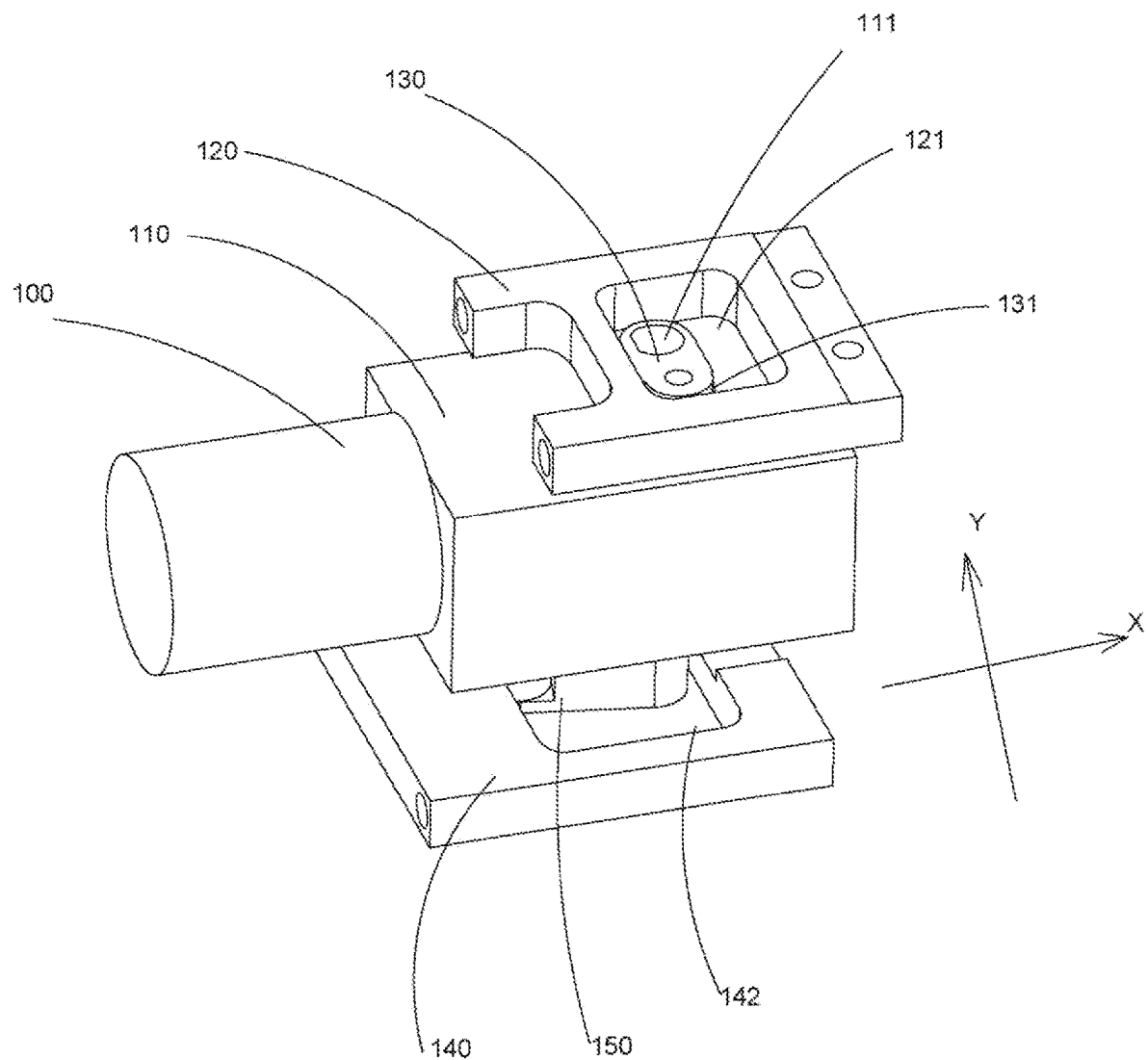
FIG. 1 is a structure schematic diagram of a driving structure.

NUMERALS 100 driving structure; 110 driving device; 111 first output end; 112 second output end; 120 first moving block; 121 first through hole; 130 first swinging block; 131 first pulley; 140 second moving block; 142 second through hole; 150 second swinging block; 151 second pulley; 160 first track; 170 second track; 200 liquid storage tank; 210 first liquid storage tank; 220 second liquid storage tank; 300 pump body; 400 feed inlet; 410 first feed inlet; 420 second feed inlet; 500 clamping block; 510 first bayonet; 600 pushing block; 610 second bayonet; 620 third bayonet; 630 limiting groove; 700 outer tube; 700 wearing device; 710 wearing structure; 720 limiting sleeve; 730 triggering device; 740 injection device; 740a first injection device; 740b second injection device; 741 needle; 741a first needle; 741b second needle; 750 first clamping groove; 760 second clamping groove; 800 working portion; 810 outlet hole; 811 first outlet hole; 812 second outlet hole; 820 first bracket; 830 second bracket; 840 arc plane; 850 first inclined plane; 860 second inclined plane; 900 driving member; 1000 limiting block; 1010 first limiting block; 1020 second limiting block; 1100 infusion tube; 1200 pump body; 1300 frame body; 1400 elastic structure; 1500 compression bar; 1600 connecting block; 1700 reset spring; 1800 first connecting rod; and 1900 second connecting rod.

DETAILED DESCRIPTION

The concept and the generated technical effect of the present invention are clearly and completely described hereinafter with reference to the embodiments to fully understand the objectives, the features and the effects of the present invention. Apparently, the described embodiments are only some but not all of the embodiments of the present invention, and based on the embodiments of the present invention, other embodiments obtained by those skilled in the art without going through any creative work all belong to the scope of protection of the present invention.

In the description of the embodiments of the present invention, the orientation or position relationship indicated by the terms "up", "down", "front", "rear", "left", "right", and the like is based on the orientation or position relationship shown in the accompanying drawings, it is only for the convenience of description of the present invention and simplification of the description, and it is not to indicate or imply that the indicated device or element must have a specific orientation, and be constructed and operated in a specific orientation. Therefore, the terms shall not be understood as limiting the present invention.

In the description of the embodiments of the present invention, if some feature is called "set", "fixed", "connected" or "installed" on another feature, the feature may be directly set, fixed or connected to another feature, or indirectly set, fixed, connected or installed on another feature. In the description of the embodiments of the present invention, the meaning of "several" refers to be one or more, and the meaning of "multiple" refers to be more than two. The meanings of "greater than", "less than", "more than", and the like shall be understood as not including this number, while the meanings of "above", "below", "within", and the like shall be understood as including this number. The terms "first" and "second" shall be understood as being used for distinguishing the technical features only in the description, and cannot be understood as indicating or implying relative importance, implicitly indicating the number of technical features indicated thereby, or implicitly indicating the order of technical features indicated thereby.

First Embodiment of Driving Structure 100

As shown in FIG. 1, a driving structure 100 includes a driving device 110, a first swinging assembly and a second swinging assembly. The driving device 110 is provided with a first output end 111 and a second output end 112, the first swinging assembly includes a first moving block 120 and a first swinging block 130, and the second moving assembly includes a second moving block 140 and a second swinging block 150. The first output end 111 of the driving device 110 is connected with the first swinging block 130, and the other side of the first swinging block 130 relative to the first output end 111 acts on the first moving block 120 and drives the first moving block 120 to move. The second output end 112 of the driving device 110 is connected with the second swinging block 150, and the other side of the second swinging block 150 relative to the second output end 112 acts on the second moving block 140 and drives the second moving block 140 to move. The first moving block 120 and the second moving block 140 are driven by one driving mechanism through the mechanism.

In the above structure, a time difference exists between running time of the first swinging block 130 and running time of the second swinging block 150, so that a stroke difference exists between the first moving block 120 and the second moving block 140 driven by the first swinging block 130 and the second swinging block 150, which means that movements of the first moving block 120 and the second moving block 140 are not synchronized, with a certain stroke displacement difference therebetween.

Second Embodiment of Driving Structure

The technical features added in the second embodiment based on the first embodiment are as follows. The first swinging block 130 is provided with a first fixed end and a first movable end, and the first moving block 120 is provided with a first through hole 121. The first swinging block 130 is located in the first through hole 121, the first fixed end of the first swinging block 130 is connected with the first output end 111 of the driving device 110, and the first movable end of the first swinging block 130 is provided with a first roller. When the driving device 110 starts to work, the first output end 111 of the driving device 110 drives the first swinging block 130 to rotate around the first fixed end, so that the first roller located on the first movable end rotates around an inner wall of the first through hole 121, thus driving the first moving block 120 to move through rotation of the first swinging block 130. The second swinging block 150 is provided with a second fixed end and a second movable end, and the second moving block 140 is provided with a second through hole 142. The second swinging block 150 is located in the second through hole 142, the second fixed end of the second swinging block 150 is connected with the second output end 112 of the driving device 110, and the second movable end of the second swinging block 150 is provided with a second roller. When the driving device 110 starts to work, the second output end 112 of the driving device 110 drives the second swinging block 150 to rotate around the second fixed end, so that the second roller located on the second movable end rotates around an inner wall of the second through hole 142, thus driving the second swinging block 150 to rotate and driving the second moving block 140 to move.

Figure 2:
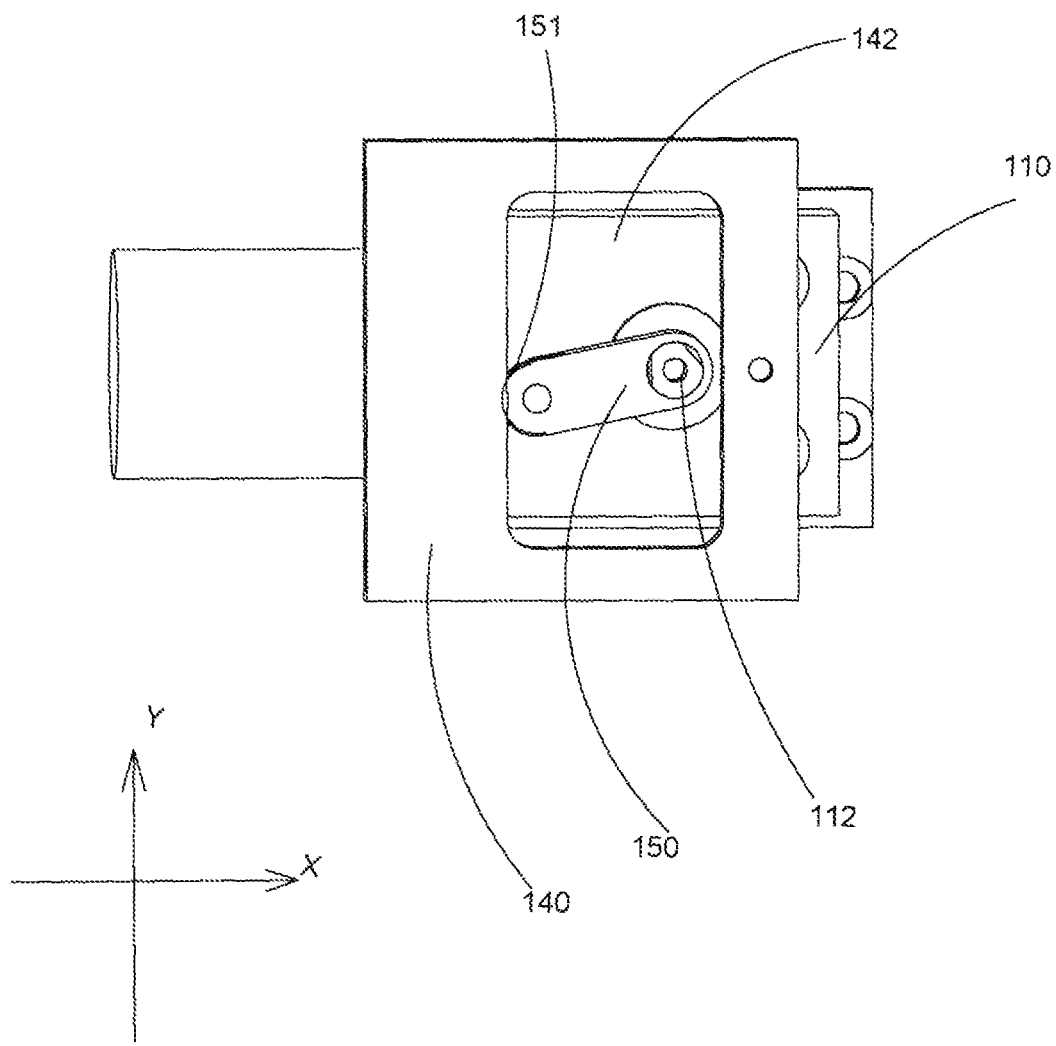
FIG. 2 is a bottom view of FIG. 1.

As shown in FIG. 1 and FIG. 2, a length of the first through hole 121 on an X-axis is greater than or equal to a length of the first swinging block 130, which is less than or equal to a length of two first swinging blocks 130. When the movable end of the first swinging block 130 is located at a lowest end in a Y-axis direction (which is namely a position shown in FIG. 1), and the first swinging block 130 moves clockwise, the first moving block 120 can only move to the left through a force given to the first movable end by the first fixed end until the first swinging block 130 rotates clockwise by 90°. At the moment, the first swinging block 130 is located at a leftmost end in an X-axis direction. When the first swinging block 130 rotates clockwise, the length of the first through hole 121 in the Y-axis direction is greater than or equal to the length of two first swinging blocks 130, so that a position of the first moving block 120 remains unchanged. The first moving block 120 is driven by the driving device 110 through the above structure. A driving mode of the second moving block 140 is the same as that of the first moving block 120. As shown in FIG. 2, when the movable end of the second swinging block 150 is located at a bottom end in the Y-axis direction, and the second swinging block 150 moves clockwise, the second swinging block 140 can only move to the left through a force given to the second movable end by the second fixed end until the second swinging block 150 rotates clockwise by 90°. When the movable end of the second swinging block 150 is located at the leftmost end in the X-axis direction, and the second swinging block 150 rotates clockwise, since a length of the second through hole 142 in the Y-axis direction is greater than or equal to a length of two second swinging blocks 150, a position of the second swinging block 140 remains unchanged.

Third Embodiment of Driving Structure

Figure 3:
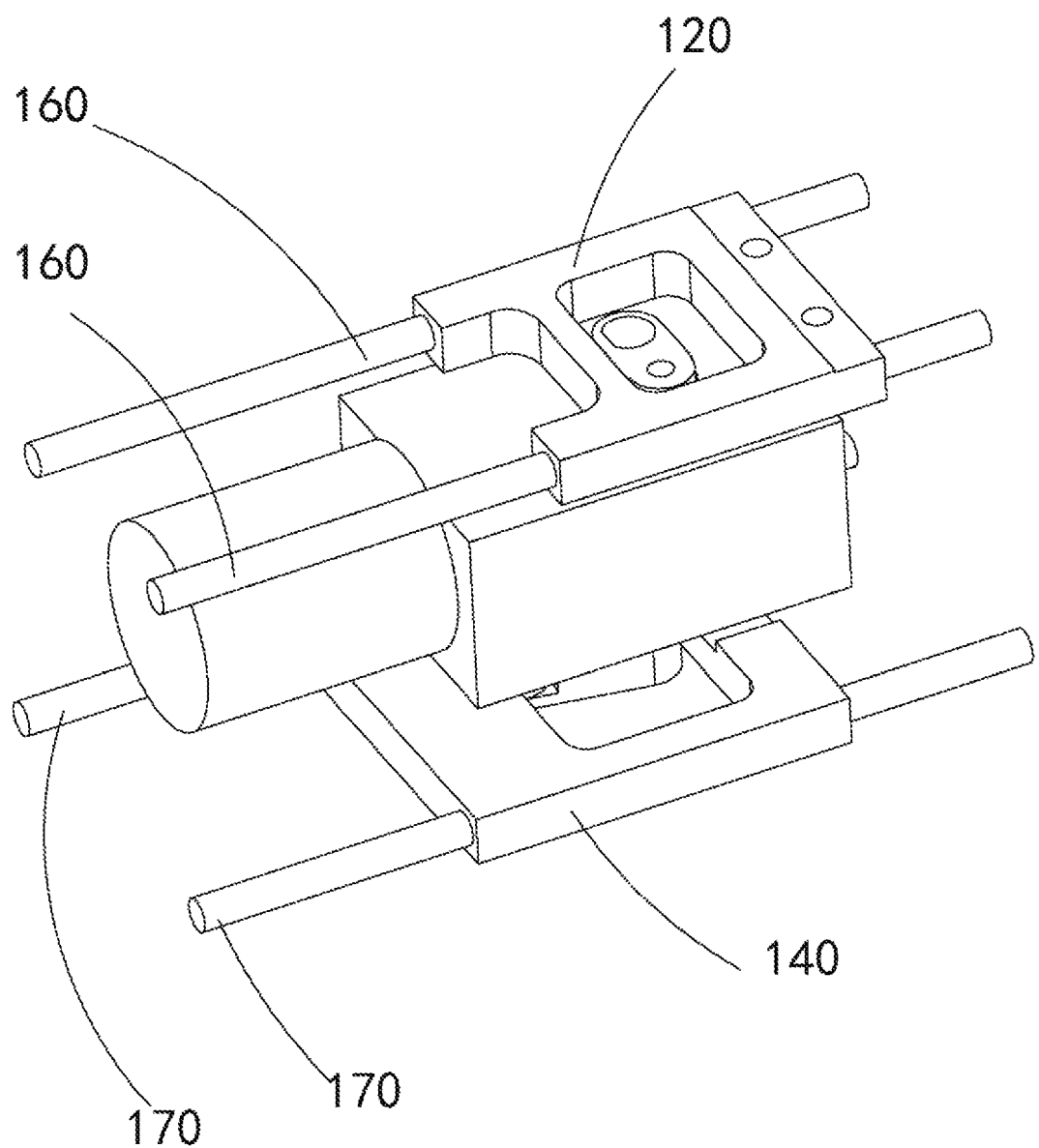
FIG. 3 is a structure diagram of another embodiment of the driving structure.

The technical features added in the third embodiment based on the first embodiment and the second embodiment are as follows. As shown in FIG. 3, the driving structure further includes a first track 160 and a second track 170. The first track 160 penetrates through the first moving block 120, the first moving block 120 is capable of moving along the first track 160, the second track 170 penetrates through the second moving block 140, and the second moving block 140 is capable of moving along the second track 170. The first track 160 and the second track 170 are parallel, so that the first moving block 120 and the second moving block 140 move alternately on the first track 160 and the second track 170 respectively.

The embodiment further includes a mode that the first moving block 120 is capable of moving along the first track 160 as a slider. Similarly, the second moving block 140 is capable of moving along the second track 170 as a slider, so that the first moving block 120 and the second moving block 140 move alternately along the first track 160 and the second track 170 respectively.

Fourth Embodiment of Driving Structure

The technical features added in the fourth embodiment based on the first to third embodiments are as follows. An angle difference between the second swinging block and the first swinging block ranges from 80° to 180°. According to the angle difference, when the first swinging block and the second swinging block both rotate clockwise, the second moving block 140 is located in front of the first moving block 120 during both forward movement in the X-axis direction and reverse movement in the X-axis direction, which means that the first moving block 120 and the second moving block 140 reciprocate along the X-axis, and the second moving block 140 always moves before the first moving block 120.

Fifth Embodiment of Driving Structure

The technical features added in the fifth embodiment based on the first embodiment are as follows. The first swinging assembly and the second swinging assembly are both in a crank-slider structure, the first swinging block 130 and the second swinging block 150 are both crank mechanisms, and the first moving block 120 and the second moving block 140 are both in a slider structure. The first moving block 120 and the second moving block 140 are capable of being driven to move by swinging the first swinging block 130 and the second swinging block 150 through the structure.

Sixth Embodiment of Driving Structure

The sixth embodiment is different from the first embodiment in that, in the sixth embodiment, the driving device 110 only includes one output end, and the first swinging assembly and the second swinging assembly are both located on a same output end. However, in the structure, the first swinging block 130 and the second swinging block 150 are arranged by different angles, so that an angle difference exists between swinging of the first swinging block 130 and swinging of the second swinging block 150, thus having a stroke difference between the first moving block 120 driven by the first swinging block 130 and the second moving block 140 driven by the second swinging block 150.

First Embodiment of Injection Machine

Figure 4:
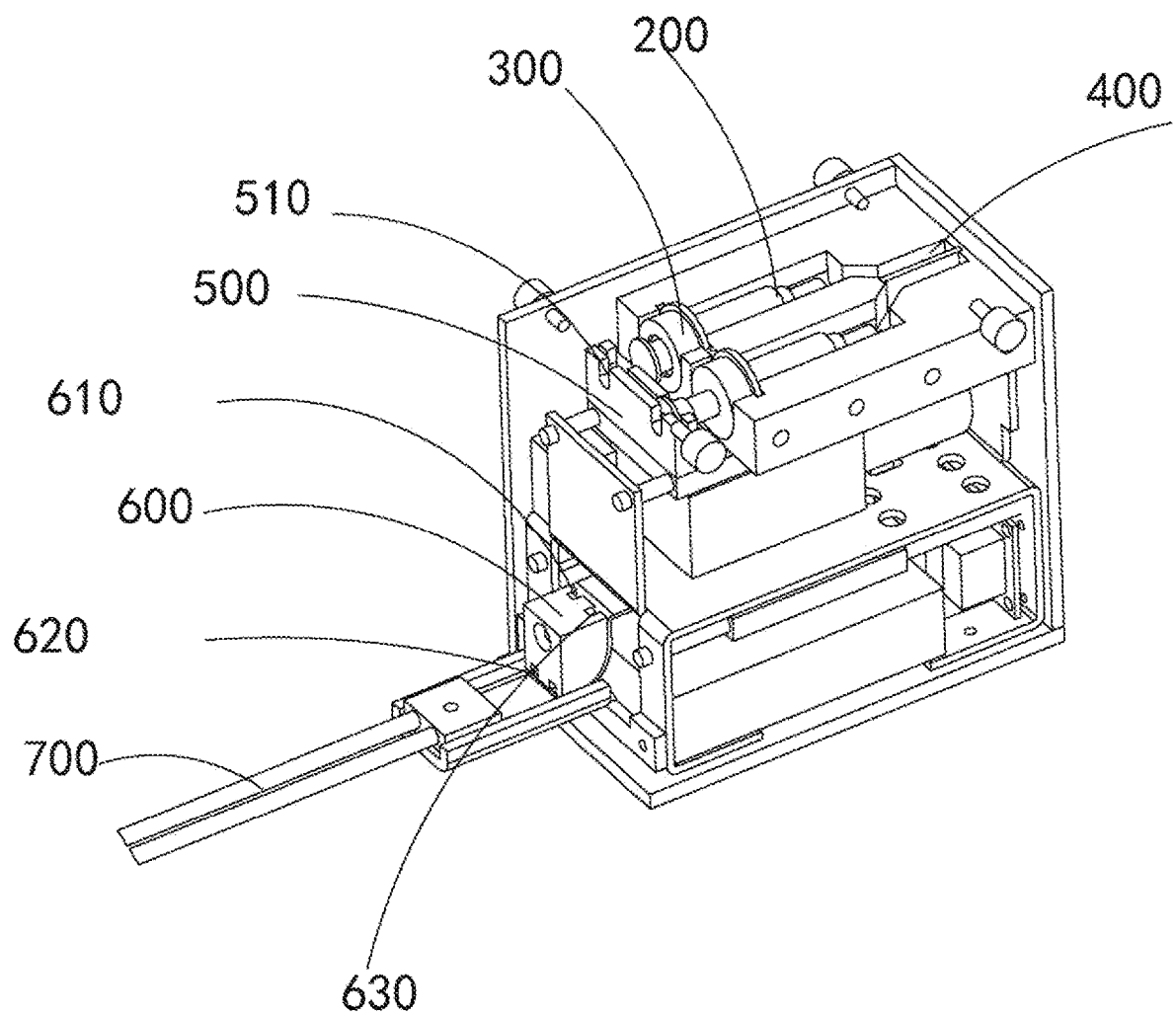
FIG. 4 is a diagram of an embodiment of an injection machine.
Figure 5:
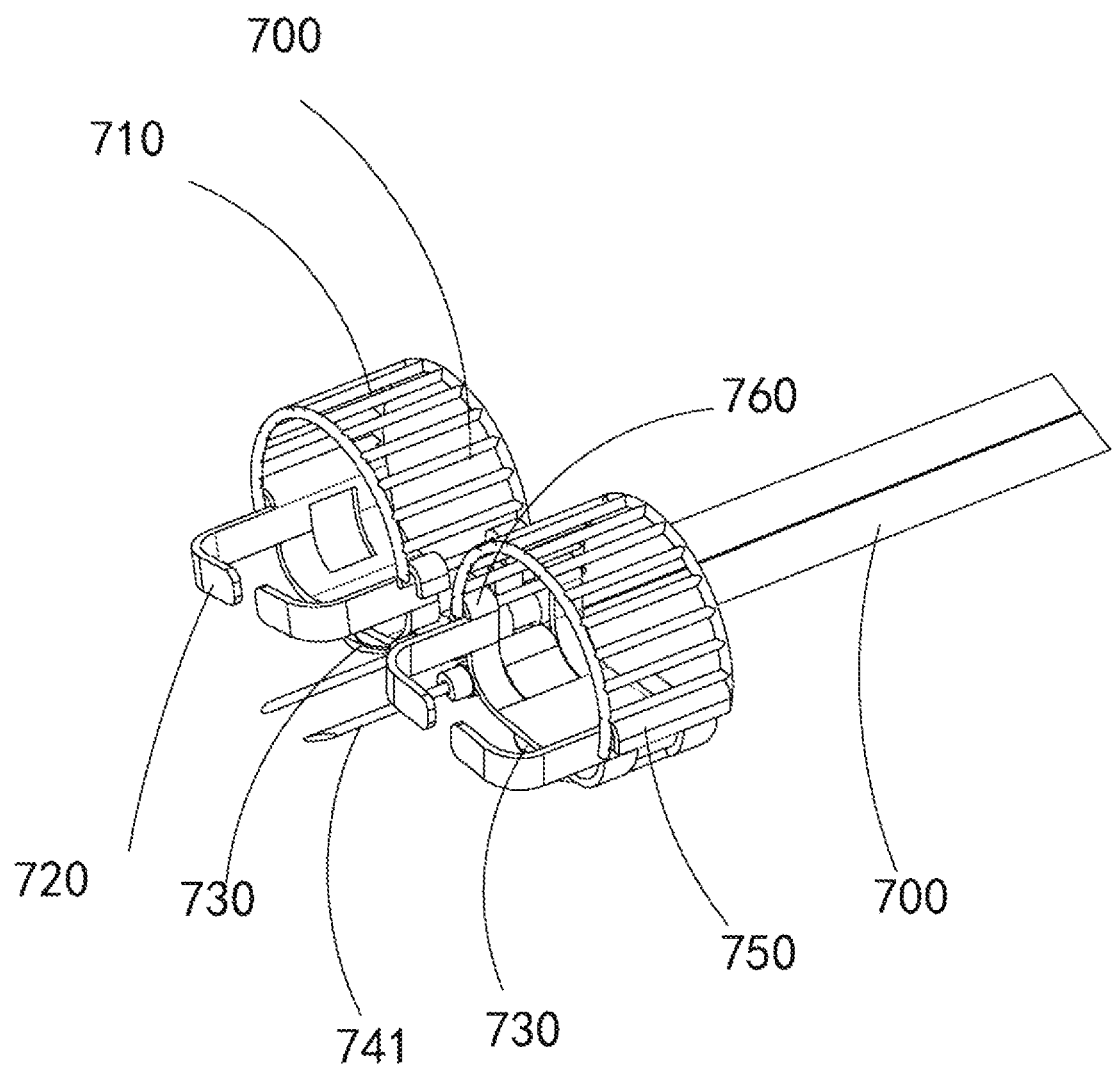
FIG. 5 is a structure diagram of a wearing structure.

In the embodiment, as shown in FIG. 4 and FIG. 5, the injection machine includes a liquid storage tank 200, a needle 741 (not shown) and the driving structure 100 described above. The liquid storage tank 200 is used for storing a liquid, and the liquid storage tank 200 is connected with an inlet of the needle 741. The needle 741 is used for injecting the liquid in the liquid storage tank 200 into an object to be injected.

The first embodiment of the injection device includes but is not limited to a solution of injecting the liquid into the needle 741 through a gravity of the liquid in the liquid storage tank 200.

Second Embodiment of Injection Machine

The technical features added in the second embodiment of the injection machine based on the first embodiment are as follows. As shown in FIG. 4, the injection machine further includes a pushing block 600 and an infusion tube (not shown). One end of the infusion tube is connected with the outlet of the liquid storage tank 200, and the other end of the infusion tube is connected with the inlet of the needle 741. The pushing block 600 is provided with a limiting groove 630 (not shown), and a part of infusion tube is located in the limiting groove 630. The limiting groove 630 is provided with a second bayonet 610 and a third bayonet 620, and the limiting groove 630 is arranged between the second bayonet 610 and the third bayonet 620. The infusion tube 1100 is located in the channel and is limited by the limiting groove 630. The pushing block 600 is connected with the second moving block 140, and the second moving block 140 drives the pushing block 600 to move. Meanwhile, the infusion tube connected with the pushing block 600 is driven to move, and the needle 741 connected with the infusion tube is driven to move, thus driving the needle 741 to complete a penetrating action.

A pump body 300 moves to convey the liquid in the liquid storage tank 200 into the needle 741 through the infusion tube. Meanwhile, the liquid in the outside is capable of entering the liquid storage tank 200 through a feed inlet 400 by movement of the pump body 300, thus supplementing the liquid in the liquid storage tank 200.

In the above structure, a stroke of the second moving block 140 occurs before a stroke of the first moving block 120. Since the second moving block 140 is formed before the first moving block 120, the penetrating action of the needle 741 and liquid pumping are not synchronized in the structure of the injection machine. The second moving block 140 moves along the second track 170 through driving of the driving device 110, thus driving the pushing block 600 to move, so that the infusion tube limited in the pushing block 600 moves forwardly, and the needle 741 is penetrated into a body of the object to be injected. Meanwhile, the first swinging block 130 swings ceaselessly, so that the first moving block 120 moves towards a moving direction of the second moving block 140, thus driving the pump body 300 to move, conveying the liquid from the liquid storage tank 200 to the needle 741 through the infusion tube, and completing injection.

It can be known from the above structure that the penetrating action of the needle 741 through driving of the driving device 110 and the injecting action may be non-synchronously completed by an operator, and the injecting action may be completed after the penetrating action. Compared with the injection device which completes the penetrating action and the injecting action at the same time, the operation mode reduces irritation to the object to be injected, enables an injection process to be milder, and makes the object to be injected difficult to be damaged.

Third Embodiment of Injection Machine

The technical features added in the third embodiment of the injection machine based on the second embodiment of the injection machine are as follows. The injection machine further includes a clamping block 500. As shown in FIG. 4, the clamping block 500 is arranged adjacent to the liquid storage tank 200, the clamping block 500 further includes a first bayonet 510, and the first bayonet 510 limits the infusion tube. One end of the infusion tube is connected with the outlet of the liquid storage tank 200, and the other end of the infusion tube penetrates through the first bayonet 510 on the clamping block 500, which is finally connected with the needle 741 after passing through the limiting groove 630 of the pushing block 600. The infusion tube 1100 inserted in the injection machine is capable of being well fixed through the clamping block 500 and the first bayonet 510 on the clamping block 500.

Fourth Embodiment of Injection Machine

The technical features added in the fourth embodiment of the injection machine based on the three embodiments of the three injection machines above are as follows. The injection machine further includes a wearing device 700. The wearing device 700 is arranged adjacent to the needle 741, and the wearing device 700 is capable of being worn on limbs of a human body, so that the operator is capable of working more conveniently during operation of the injecting action.

Fifth Embodiment of Injection Machine

The technical features added in the fifth embodiment of the injection machine based on the fourth embodiment of the injection machine are as follows. The wearing device is in a sleeve structure, and the sleeve structure includes a base and a wearing structure 710. The base includes a first clamping groove 750 and a second clamping groove 760, and is provided with at least two hooks, wherein one hook is clamped into the first clamping groove 750 and the other hook is clamped into the second clamping groove 760. The hooks are capable of being mutually separated from the first clamping groove 750 and the second clamping groove 760, so that the wearing structure 710 on the base is capable of being replaced. The structure has at least the following two technical effects: firstly, the wearing structures 710 with different lengths are capable of being replaced, so that a size of the sleeve structure is adjusted to adapt to sizes of limbs of different operators or widths of different limbs of the same operator; and secondly, an attrition degree of the wearing device 700 is reduced by replacing different wearing structures 710, thus prolonging a service life of the injection device 740.

Sixth Embodiment of Injection Machine

According to association to the fifth embodiment of the injection machine, the wearing structure 710 includes multiple hooks, and each hook is capable of being connected with the first clamping groove 750 or the second clamping groove 760, so that the size of the sleeve structure is capable of being adjusted by clamping different hooks into the first clamping groove 750 or the second clamping groove 760, thus adapting to the sizes of the limbs of different operators or the widths of different limbs of the same operator.

Seventh Embodiment of Injection Machine

According to association to the sixth embodiment of the injection machine, one end of the wearing structure 710 is fixedly connected with the first clamping groove 750, and the wearing structure 710 is also provided with multiple hooks. The size of the sleeve structure is adjusted by connecting different hooks with the second clamping groove 760, thus adapting to the sizes of the limbs of different operators or the widths of different limbs of the same operator.

Eighth Embodiment of Injection Machine

According to association to the sixth embodiment of the injection machine, the sixth embodiment is different from the second embodiment in that, as shown in FIG. 5, the wearing device 700 is in a mesh structure. In the embodiment, the mesh structure of the wearing structure 710 is formed by multiple parallel hooks.

Ninth Embodiment of Injection Machine

The technical features added in the ninth embodiment of the injection machine based on the fifth embodiment of the injection machine are as follows. The wearing structure 710 is in a "C" shape, and the operator may clamp the wearing structure 710 into the limbs of the operator through a notch of the C-shaped wearing structure 710 to complete wearing.

Tenth Embodiment of Injection Machine

As a supplement to the solution of the fourth embodiment to the ninth embodiment of the injection machine, the wearing structure 710 has a certain elastic deformation capability, and the size of the sleeve structure is appropriately adjusted by the limbs of the operator extending into the sleeve structure.

Eleventh Embodiment of Injection Machine

The technical features added in the eleventh embodiment of the injection machine based on the fourth embodiment of the injection machine to the tenth embodiment of the injection machine are as follows. The embodiment includes a limiting device, and the limiting device includes a baffle. The baffle is located on a side of the sleeve structure close to the needle 741 to complete an injection function and is located on an extending path of the limbs. The limbs of the operator extending into the sleeve structure may be blocked by the baffle through the limiting device and the baffle, so that the needle 741 protects the limbs of the operator during the injection operation, thus preventing the needle 741 from damaging the limbs of the operator during the injection operation.

Twelfth Embodiment of Injection Machine

The technical features added in the twelfth embodiment of the injection machine based on the above embodiments are as follows. The injection machine further includes an outer tube 700. The needle 741 is capable of moving in the outer tube 700, and the outer tube 700 includes a needle outlet. The needle 741 moves in the outer tube 700, so that a part of the needle 741 completing the injecting action is capable of moving relative to the outer tube 700, thus completing the injecting action.

In the above structure, as long as the needle 741 is capable of moving relative to the needle outlet, the needle 741 is capable of completing the penetrating action. In the process, the needle 741 may be completely retracted into the outer tube 700, and the needle 741 may also be partially retracted into the outer tube 700.

Thirteenth Embodiment of Injection Machine

Figure 7:
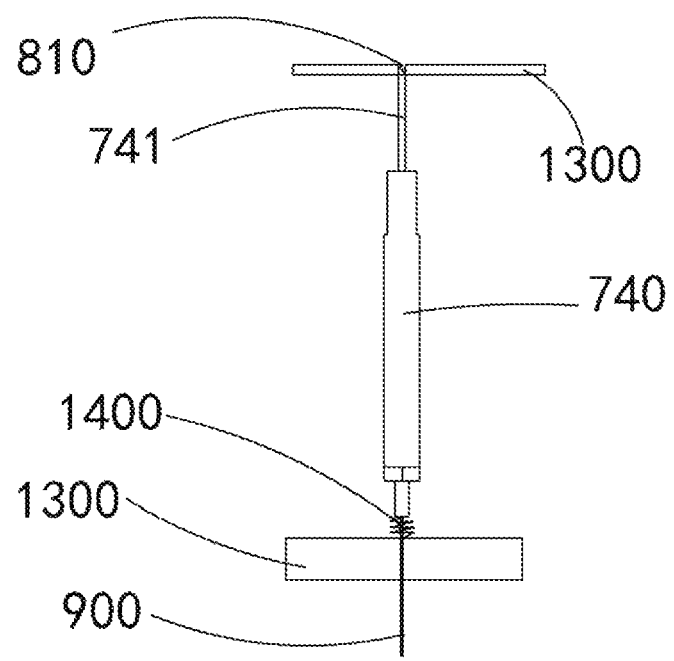
FIG. 7 is a local structure diagram of an embodiment of the injection machine.
Figure 10:
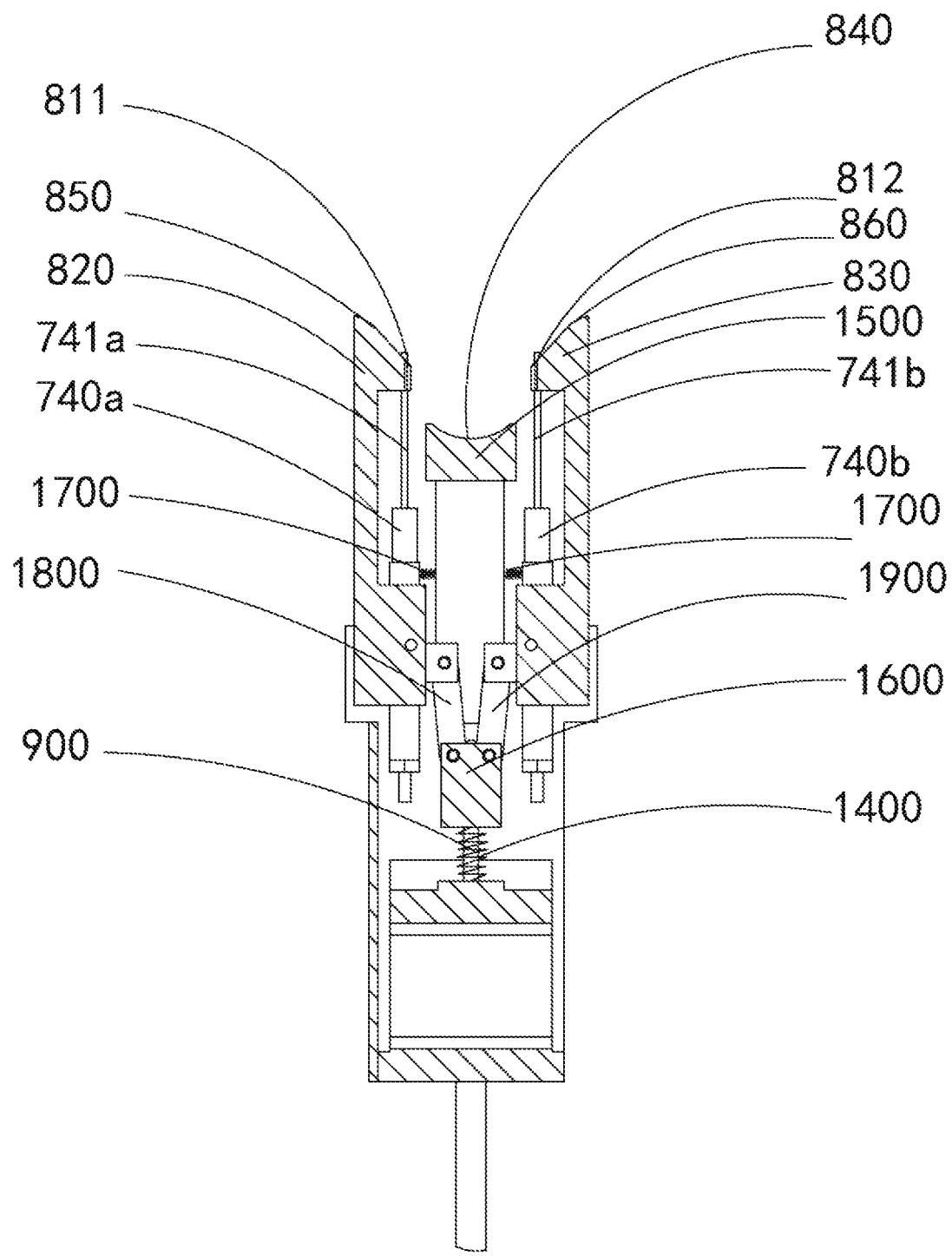
FIG. 10 is a structure diagram of a part of structure in FIG. 6.

The technical features added in the thirteenth embodiment of the injection machine based on the first embodiment of the injection machine are as follows. As shown in FIG. 7 and FIG. 10, the injection machine further includes the driving device 110 and an infusion tube 1100. The output end of the driving device 110 is connected with the second moving block 140, and the second moving block 140 is connected with the needle 741 through the infusion tube 1100. Since the infusion tube 1100 itself has a certain hardness, the needle 741 of the injection device 740 is capable of completing an inserting action by pushing the injection device 740 through the second moving block 140. The first moving block 120 is connected with the liquid storage tank 200, and the first moving block 120 drives the liquid storage tank 200 to inject the liquid from the liquid storage tank 200 into the needle 741.

The embodiment further includes a pump body (not shown), and the liquid storage tank 200 further includes a feed inlet (not shown) for supplementing the liquid into the liquid storage tank 200. The pump body is connected with the first moving block 120, and the pump body is capable of moving relative to an interior of the liquid storage tank 200 through driving of the first output end of the driving device 110, so that the liquid in the liquid storage tank 200 is conveyed into the injection device 740 through the infusion tube 1100. Meanwhile, the liquid in the outside is capable of entering the liquid storage tank 200 through the feed inlet by movement of the pump body 300, thus supplementing the liquid in the liquid storage tank 200.

Fourteenth Embodiment of Injection Machine

Figure 8:
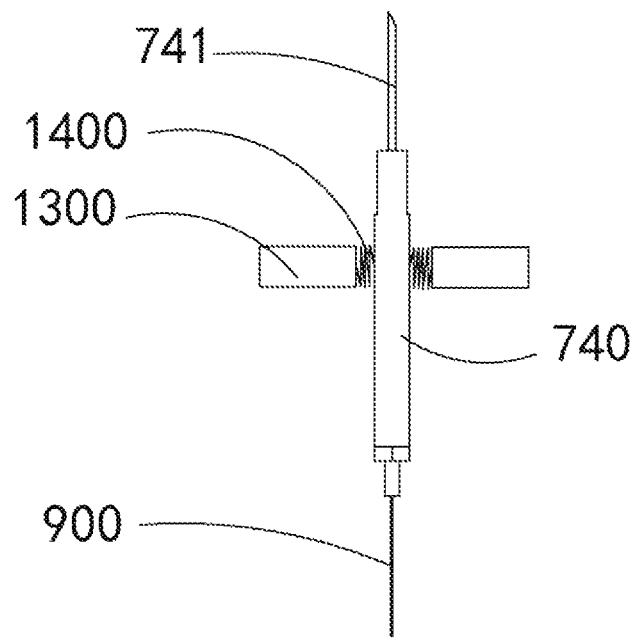
FIG. 8 is a local structure diagram of another embodiment of the injection machine.

According to association to the thirteenth embodiment of the injection machine, the fourteenth embodiment of the injection machine is different from the thirteenth embodiment of the injection machine in that, as shown in FIG. 7 and FIG. 8, the injection machine further includes a frame body 1300 and an elastic structure 1400. One end of a driving member 900 is connected with the second moving block 140, and the other end of the driving member is connected with the injection device 740. One end of the elastic structure 1400 is connected with the frame body 1300, and the other end of the elastic structure is abutted against an injector. When the driving member 900 pulls the injection device 740, the elastic structure 1400 is compressed or stretched, and when pulling to the driving member 900 is released, a force of restoring deformation of the elastic structure 1400 enables the needle 741 of the injection device 740 to complete the penetrating action.

In the embodiment, a position of the elastic structure 1400 is not limited, as long as the force capable of restoring the deformation thereof may adapt to the injection device 740 to complete the injecting action.

As shown in FIG. 7, the frame body 1300 includes a gap, and the driving member 900 penetrates through the gap. One end of the injection device 740 is abutted against the frame body 1300 through the elastic structure 1400. When the second moving block 140 drives the driving member 900 to move downwardly as shown in the drawing, which means that the needle 741 extends outwardly from the frame body 1300 and is retracted into the frame body 1300, the elastic structure 1400 is compressed in the process. A pulling force on the driving member 900 is reduced during rotation of the second moving block 140, so that the force of restoring deformation of the elastic structure 1400 enables the needle 741 to penetrate outwardly.

Alternatively, as shown in FIG. 8, when the injection device 740 is stretched downwardly as shown in the drawing through the driving member 900, the elastic structure 1400 is stretched. At the moment, the needle 741 is converted from outward extension from the frame body 1300 to retraction into the frame body 1300. The driving member 900 does not stretch the injection device 740 during rotation of the second rotating block, so that the force of restoring deformation of the elastic structure 1400 enables the needle 741 to complete the penetrating action.

Fifteenth Embodiment of Injection Machine

Figure 9:
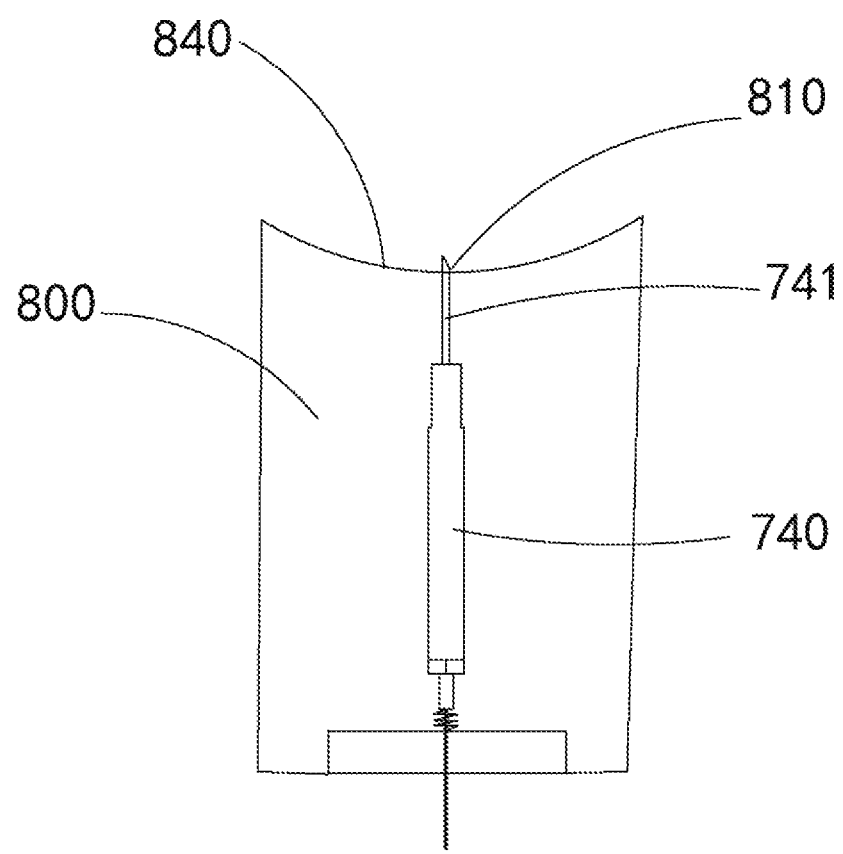
FIG. 9 is a local structure diagram of another embodiment of the injection machine.

The technical features added in the fifteenth embodiment of the injection machine based on the thirteenth embodiment of the injection machine and the fourteenth embodiment of the injection machine are as follows. As shown in FIG. 9, the injection machine further includes a working portion 800, and the working portion 800 includes an arc-shaped contact surface. The arc-shaped contact surface is used for being in contact with the object to be injected, so that the working portion 800 may be better fitted with the object to be injected. The arc-shaped contact surface is provided with an outlet hole 810, and the needle 741 of the injection device 740 is capable of protruding outwardly relative to the arc-shaped contact surface through the outlet hole 810, thus completing the penetrating action on the object to be injected.

Sixteenth Embodiment of Injection Machine

The technical features added in the sixteenth embodiment of the injection machine based on the fifteenth embodiment of the injection machine are as follows. The working portion 800 includes a first bracket 820 and a second bracket 830, and the first bracket 820 and the second bracket 830 are adjacent to each other. The first bracket 820 is provided with a first inclined plane 850, and the second bracket 830 is provided with a second inclined plane 860. The first inclined plane 850 and the second inclined plane 860 form a V-shaped structure, so that the structure may be easily fitted with the object to be injected.

In the embodiment, as shown in FIG. 10, the injection machine includes a first injection device 740a and a second injection device 740b. The first injection device 740a is connected with the first bracket 820, and the first injection device 740a is capable of moving relative to the first bracket 820, so that the first needle 741a of the first injection device 740a is capable of extending out relative to the first outlet 811 located on the first bracket 820, thus enabling the first injection device 740a to complete the penetrating action on the object to be injected. Similarly, the second injection device 740b is connected with the second bracket 830, and the second injection device 740b is capable of moving relative to the second bracket 830, so that the needle 741b of the second injection device 740b is capable of extending out relative to the second outlet hole 812 located on the second bracket 830, thus enabling the second injection device 740b to complete the penetrating action on the object to be injected.

As shown in FIG. 10, in the embodiment, the injection machine further includes a connecting block 1600, a first connecting rod 1800 and a second connecting rod 1900. One end of the first connecting rod 1800 is connected with the driving member 900, and the other end of the first connecting rod 1800 is connected with the first connecting rod 1800 and the second connecting rod 1900 at the same time. The other end of the first connecting rod 1800 relative to the connecting block 1600 is connected with the first injection device 740a, thus driving the first injection device 740a to move relative to the first bracket 820. The other end of the second connecting rod 1900 relative to the connecting block 1600 is connected with the second injection device 740b, thus driving the second injection device 740b to move relative to the second bracket 830.

Figure 6:
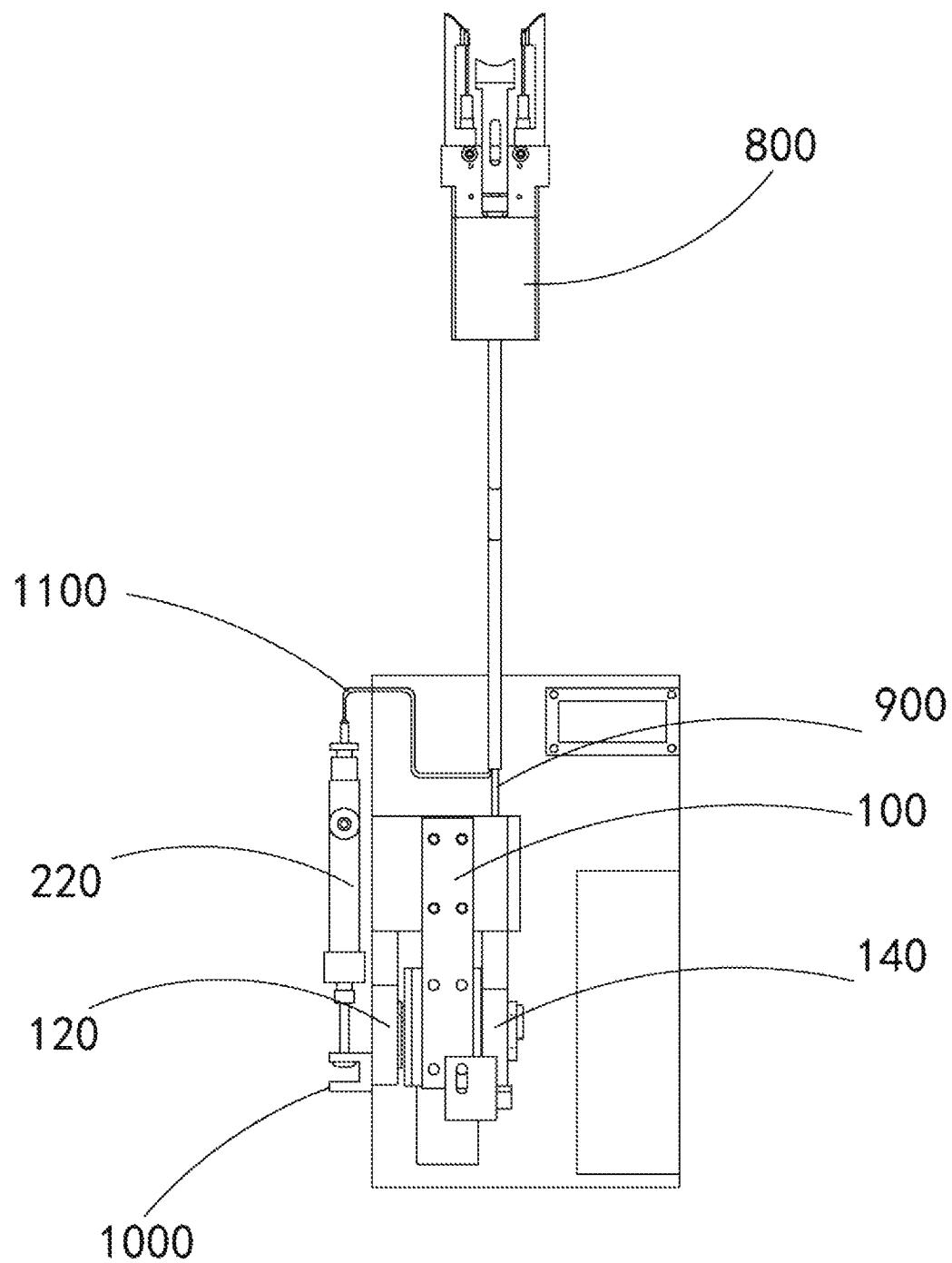
FIG. 6 is a structure diagram of another embodiment of the injection machine.

Refereeing to FIG. 6 and FIG. 7, movement of the second moving block 140 drives the driving member 900 to move through driving of the driving device 110 by the above structure. The first injection device 740a located on the first bracket 820 and the second injection device 740b located on the second bracket 830 are capable of completing the injecting action through transmission of the connecting block 1600, the first connecting rod 1800 and the second connecting rod 1900.

Seventeenth Embodiment of Injection Machine

As shown in FIG. 10, the technical features added in the seventeenth embodiment of the injection machine based on the sixteenth embodiment of the injection machine are as follows. The working portion 800 further includes a compression bar 1500. The first bracket 820 and the second bracket 830 are respectively arranged at two sides of the compression bar 1500. An end of the compression bar 1500 adjacent to the first inclined plane 850 and the second inclined plane 860 is provided with the arc plane 840, and the arc-shaped contact surface is composed of the first inclined plane 850, the arc plane 840 and the second inclined plane 860 jointly. The arc-shaped contact surface is capable of being better in contact with the object to be injected.

Eighteenth Embodiment of Injection Machine

The technical features added in the eighteenth embodiment of the injection machine based on the seventeenth embodiment of the injection machine are as follows. The first bracket 820 and the second bracket 830 are both capable of rotating relative to the compression bar 1500. As shown in FIG. 10, the first bracket 820 is capable of rotating counterclockwise relative to the compression bar 1500, and the second bracket 830 is capable of rotating clockwise relative to the compression bar 1500, so that the first inclined plane 850 on the first bracket 820, the second inclined plane 860 on the second bracket 830 and the arc plane 840 on the compression bar 1500 after rotation form a relatively smooth arc plane structure, thus being better in contact with the object to be injected.

In the embodiment, when the first bracket 820 and the second bracket 830 rotate relative to the compression bar 1500, the first injection device 740a located on the first bracket 820 and the second injection device 740b located on the second bracket 830 also rotate along with the first bracket 820 and the second bracket 830 respectively, so that a first injector and a second injector may be inclined by a certain angle relative to the object to be injected during injection, thus preventing damage to the body of the object to be injected during vertical penetration.

Nineteenth Embodiment of Injection Machine

The technical features added in the nineteenth embodiment of the injection machine based on the embodiments of the injection machine above are as follows. As shown in FIG. 10, the injection machine further includes a reset spring 1700. The reset spring 1700 is arranged between the first bracket 820 and the compression bar 1500, and the reset spring 1700 is also arranged between the second bracket 830 and the compression bar 1500. When the object to be injected leaves the compression bar 1500, the first bracket 820 and the second bracket 830, and the object to be injected leaves the first inclined plane 850, the second inclined plane 860 and the arc plane 840, the first bracket 820 and the second bracket 830 are capable of being restored to an initial device through the reset spring 1700, which is namely a state shown in FIG. 7.

In the above structure, the reset spring 1700 also has a beneficial effect that since the first bracket 820 and the second bracket 830 are both connected with the compression bar 1500 through the reset spring 1700, when the object to be injected is in contact with the first inclined plane 850 and the second inclined plane 860, the first inclined plane 850 and the second inclined plane 860 both give an action of a certain force to the object to be contacted, so that the first inclined plane 850 and the second inclined plane 860 are in contact with the object to be injected more closely, which is beneficial for injection of the first injection device 740a and the second injection device 740b. Meanwhile, since the first bracket 820 and the second bracket 830 are in contact with the compression bar 1500 through the reset spring 1700, a pressure applied to the object to be injected by a first compression bar 1500 and a second compression bar 1500 is limited, without causing too much squeezing force on the object to be injected in a recession formed by the first inclined plane 850, the second inclined plane 860 and the arc plane 840, thus ensuring a safety of the object to be injected.

Twentieth Embodiment of Injection Machine

The technical features added in the twentieth embodiment of the injection machine based on the embodiments of the injection machine above are as follows. The injection machine further includes a triggering device 730. The triggering device 730 is located on the working portion 800 for being in contact with the object to be injected, and the triggering device 730 is electrically connected with the driving device 110. When the triggering device 730 is in contact with the object to be injected, the triggering device 730 is triggered, then the driving device 110 electrically connected with the triggering device 730 starts to work, and then the first moving block 120 and the second moving block 140 move to complete the penetrating action and the injecting action of the injection device 740.

Twenty-First Embodiment of Injection Machine

The technical features added in the twenty-first embodiment of the injection machine based on the seventeenth embodiment of the injection machine or the eighteenth embodiment of the injection machine are as follows. The triggering device 730 may be located on the first inclined plane 850 of the first bracket 820, the second inclined plane 860 of the second bracket 830 or the arc plane 840 of the compression bar 1500.

Twenty-Second Embodiment of Injection Machine

The technical features added in the twenty-second embodiment of the injection machine based on the twenty-first embodiment of the injection machine are as follows. The triggering device 730 is located on a side of the connecting block 1600 close to the compression bar 1500. When the compression bar 1500 is squeezed by the object to be injected, the compression bar 1500 moving downwardly as shown in FIG. 10 may trigger the triggering device 730, thus driving the driving structure 100 to move, and enabling the injection device 740 to complete the penetrating action and the injecting action.

Twenty-Third Embodiment of Injection Machine

The twenty-third embodiment of the injection machine is different from the second embodiment of the injection machine in that, in the second embodiment of the injection device 740, the liquid is capable of being conveyed into the object to be injected through movement of the pump body 300. In the embodiment, a tank body of the liquid storage tank 200 is capable of being deformed to change a volume of the liquid storage tank 200, and a pressure in the liquid storage tank 200 is changed by changing the volume of the liquid storage tank 200 itself. When the volume of the liquid storage tank 200 is reduced, an internal space of the liquid storage tank 200 is squeezed, and an internal liquid enters the injection device 740 from the outlet of the liquid storage tank 200. When the volume of the liquid storage tank 200 is restored, an external liquid enters the liquid storage tank 200 through the feed inlet 400, thus completing supplementation of the liquid storage tank 200.

Twenty-Fourth Embodiment of Injection Machine

The twenty-fourth embodiment of the injection machine is different from the second embodiment of the injection machine and the twenty-third embodiment of injection machine in that, in the second embodiment of the injection machine and the thirteenth embodiment of the injection machine, the liquid storage tank 200 is supplemented through the feed inlet 400. In the thirteenth embodiment of the injection device 740, the feed inlet 400 is not provided, and the liquid storage tank 200 is replaceable, which is a disposable product. The liquid storage tank 200 is detachably connected with the injection device 740, so that the liquid storage tank 200 is replaced after the liquid in one liquid storage tank 200 is completely injected.

Twenty-Fifth Embodiment of Injection Machine

Figure 11:
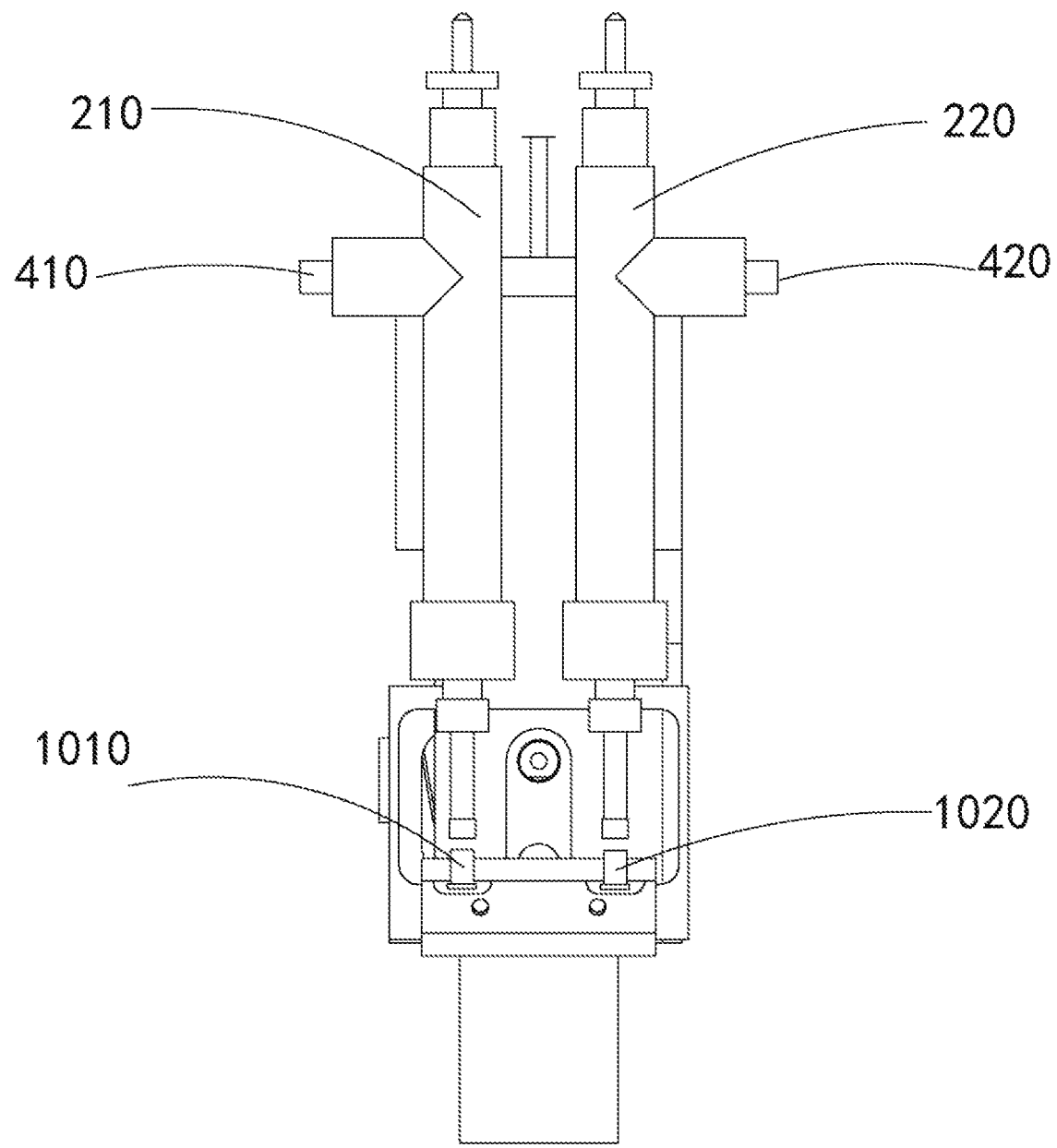
FIG. 11 is a structure diagram of a part of structure of a liquid storage tank in FIG. 6.

As shown in FIG. 8 and FIG. 11, the technical features added in the twenty-fifth embodiment of the injection machine based on the twenty-fourth embodiment of the injection machine are as follows. The injection machine further includes a limiting block 1000, and the limiting block 1000 is used for limiting the pump body 300, so that a side of the pump body 300 located outside the liquid storage tank 200 may be limited by the limiting block 1000 during moving, thus limiting a stroke of the pump body 300, and adjusting a volume of the liquid injected into the needle 741 through the pump body 300.

Twenty-Sixth Embodiment of Injection Machine

With reference to FIG. 4, FIG. 10 and FIG. 11, the technical features added based on the second embodiment of the injection machine and the thirteenth embodiment of the injection machine are as follows. The machine includes two injection devices 740, which are respectively a first injection device 740*a* and a second injection device 740*b*, two limiting blocks 1000, which are a first limiting block 1010 and a second limiting block 1020, and two liquid storage tanks 200, which are a first liquid storage tank 210 and a second liquid storage tank 220. The first liquid storage tank 210 includes a first feed inlet 410, and the second liquid storage tank 220 includes a second feed inlet 420. The first liquid storage tank 210 is connected with the first injection device 740*a* through a first infusion tube, and the second liquid storage tank 220 is connected with the second injection device 740*b* through a second infusion tube. Since the first injection device 740*a* and the second injection device 740*b* are both connected with the second moving block 140, the first injection device 740*a* and the second injection device 740*b* may inject different vaccines into the object to be injected through the structure.

Twenty-Seventh Embodiment of Injection Machine

The technical features added in the twenty-seventh embodiment of the injection machine based on the embodiments of the injection machine above are as follows. With reference to FIG. 10, the object to be injected is a poultry. When a chest of the poultry is pressed against the arc plane 840 of the compression bar 1500, the first injection device 740*a* and the second injection device 740*b* are pushed by the connecting block 1600, the first connecting rod 1800 and the second connecting rod 1900 by driving the driving member 900 by the second moving block through driving of the driving device 110. Meanwhile, a pushing force of the first connecting rod 1800 and the second connecting rod 1900 enables the first bracket 820 and the second bracket 830 to start to rotate relative to the compression bar 1500, so that the first inclined plane 850, the second inclined plane 860 and the arc plane 840 form a recession, and the poultry is just located in the recession. Meanwhile, a chest of one side of a first poultry is just fitted with the first inclined plane 850, and a chest of the other side is fitted with a chest of a second side. At the moment, a liquid is injected into the chests of both sides of the poultry through the first injection device 740*a* and the second injection device 740*b*, so that the needle 741 of the first injection device 740*a* and the needle 741 of the second injection device are capable of being obliquely penetrated into the chests of both sides of the poultry, thus preventing damage to a body and/or bones of the poultry when the needle 741 of the injection device 740 is penetrated into the chest of the poultry.

The embodiments of the present invention are described in detail with reference to the accompanying drawings above, but the present invention is not limited to the above embodiments, and various changes may also be made within the knowledge scope of those of ordinary skills in the art without departing from the purpose of the present invention. In addition, the embodiments of the present invention and the features in the embodiments may be combined with each other without conflict.

What is claimed is:

1. A driving structure for driving an injection device to inject liquid, comprising: a driving device, a first swinging assembly and a second swinging assembly, wherein the first swinging assembly and the second swinging assembly both comprise a swinging block and a moving block, the swinging block is in contact with the moving block, the swinging block of the first swinging assembly and the swinging block of the second swinging assembly are both connected with an output end of the driving device, the swinging block in the same swinging assembly is configured to drive the moving block to move, and a working stroke of the moving block in the first swinging assembly and a working stroke of the moving block in the second swinging assembly are carried out at intervals;

further comprising a first track and a second track, wherein the swinging block of the first swinging assembly comprises a first swinging block, the moving block of the first swinging assembly comprises a first moving block, the swinging block of the second swinging assembly comprises a second swinging block, the moving block of the second swinging assembly comprises a second moving block, the first moving block is capable of moving along the first track, and the second moving block is capable of moving along the second track.

2. The driving structure of claim 1, wherein the driving device comprises a first output end and a second output end, the swinging block of the first swinging assembly is connected with the first output end of the driving device, and the swinging block of the second swinging assembly is connected with the second output end of the driving device.

3. The driving structure of claim 1, wherein the swinging block comprises a fixed end and a movable end, the fixed end is connected with the output end, the swinging block is capable of moving around the fixed end, and the movable end is used for driving the moving block to move.

4. The driving structure of claim 3, wherein the fixed end is provided with a roller, the moving block is provided with a through hole, the swinging block is located in the through hole, and the swinging block is connected with an inner wall of the through hole through the roller for driving the moving block to move.

5. The driving structure of claim 1, wherein an angle difference between the swinging block of the second swinging assembly and the swinging block of the first swinging assembly ranges from 80° to 180°.

6. The driving structure of claim 4, wherein a length of the through hole in an X-axis direction is greater than or equal to a distance between the fixed end and the movable end and less than or equal to twice the distance between the fixed end and the movable end, and a length of the through hole in a Y-axis direction is greater than or equal to twice the distance between the fixed end and the movable end.

7. An injection machine, comprising an injection device, a liquid storage tank and the driving structure of claim 1, wherein an outlet of the liquid storage tank is communicated with an inlet of the injection device, the liquid storage tank is used for conveying liquid into the injection device, and the driving structure is used for driving the injection device to complete a penetrating action and an injecting action.

8. The injection machine of claim 7, further comprising a pushing block and an infusion tube, wherein one end of the infusion tube is connected with the liquid storage tank, the other end of the outlet of the infusion tube is connected with the inlet of the injection device, the pushing block is provided with a limiting groove, at least a part of the infusion tube is located in the limiting groove, the pushing block is connected with the second moving block, and the second moving block is configured to drive the pushing block to move to drive the injection device to complete the penetrating action.

9. The injection machine of claim 7, further comprising a wearing device, wherein the injection device is connected with the wearing device and is configured to move relative to the wearing device.

10. The injection machine of claim 9, wherein the wearing device comprises a sleeve structure for being sheathed with limbs, and the sleeve structure is capable of being deformed to adjust a diameter thereof.

11. The injection machine of claim 10, wherein the sleeve structure comprises a base and a wearing structure, at least two clamping grooves are arranged on the wearing structure in a length direction, a hook is arranged on the base, one end of the wearing structure is connected with the base, and the other end of the wearing structure is clamped on the hook through the clamping grooves;

or, the sleeve structure comprises a base and a wearing structure, at least two clamping grooves are arranged on the wearing structure in a length direction, two hooks are arranged on the base, one end of the wearing structure is clamped on one hook through one clamping groove, and the other end of the wearing structure is clamped on the other hook through the other clamping groove.

12. The injection machine of claim 10, further comprising a limiting device, wherein the injection device comprises a needle, the limiting device comprises a baffle, and the baffle is located on a side of the sleeve structure close to the needle and located on a path where the limbs extend out.

13. The injection machine of claim 9, further comprising a triggering device, wherein the triggering device is connected with the wearing device, the triggering device is electrically connected with the driving device, and an output end of the driving device is connected with the injection device;

or, the injection machine further comprises a triggering device and the driving device, the triggering device is connected with the injection device, the triggering device is electrically connected with the driving device, and an output end of the driving device is connected with the injection device.

14. The injection machine of claim 7, further comprising a driving member and the injection device, wherein one end of the driving member is connected with the second moving block, the other end of the driving member is connected with an injector, and the injector is pushed through the second moving block to complete the penetrating action of the injector relative to an object;

or, the injection machine further comprises a frame body, a driving member and an elastic structure, one end of the driving member is connected with the second moving block, the other end of the driving member is connected with an injector, one end of the elastic structure is connected with the frame body, the other end of the elastic structure is abutted against the injector, when the driving member pulls the injection device, the elastic structure is compressed or stretched, and a force of restoring deformation of the elastic structure is used for completing the penetrating action of the injector relative to an object.

15. The injection machine of claim 7, further comprising a working portion, wherein the working portion comprises an arc-shaped contact surface, the arc-shaped contact surface is used for being in contact with the object, the arc-shaped contact surface is provided with an outlet hole, and the needle of the injection device of the injector is capable of extending out of the outlet hole to the working portion.

16. The injection machine of claim 15, further comprising the working portion which comprises a first bracket and a second bracket, wherein the first bracket comprises a first inclined plane, the second bracket comprises a second inclined plane, the first bracket and the second bracket are arranged adjacently, and the first inclined plane and the second inclined plane form a V-shaped structure for supporting the object;

or, the injection machine further comprises the working portion which comprises a first bracket and a second bracket, the first bracket comprises a first inclined plane, the second bracket comprises a second inclined plane, the first bracket and the second bracket are arranged adjacently, the first inclined plane and the second inclined plane form a V-shaped structure for supporting the object, and the first bracket and the second bracket rotate relatively, thus adjusting an angle between the first inclined plane and the second inclined plane and adjusting a size of the V-shaped structure.

17. The injection machine of claim 15, further comprising a first bracket, a second bracket and a compression bar, wherein the first bracket and the second bracket are respectively located at one end of the compression bar, the first bracket comprises a first inclined plane, the second bracket comprises a second inclined plane, the compression bar comprises an arc plane, the first inclined plane, the arc plane and the second inclined plane form the arc-shaped contact surface, and the arc-shaped contact surface is used for being in contact with the object.

18. The injection machine of claim 17, wherein the first bracket and the second bracket are capable of rotating relative to the compression bar, the first bracket and the second bracket are respectively located at one end of the compression bar, the first bracket comprises the first inclined plane, the second bracket comprises the second inclined plane, the compression bar comprises the arc plane, and when the first bracket and the second bracket are located on positions far away from the compression bar, the first inclined plane, the second inclined plane and the arc plane form the arc-shaped contact surface.

19. The injection machine of claim 17, further comprising a triggering device, a connecting block and a connecting rod, wherein one end of the connecting block is connected with an output end of the driving device, the other end of the connecting block is rotatably connected with the connecting rod, an end of the connecting rod far away from the connecting block is connected with the injection device, the triggering device is located on a side of the connecting block close to the compression bar, and when the driving member drives the compression bar to move, the triggering device is capable of being triggered; and the triggering device is located on the first inclined plane, the second inclined plane or the arc plane.

20. The injection machine of claim 18, further comprising a first injector, a second injector, a first connecting rod, a second connecting rod and a connecting block, wherein one end of the connecting block is connected with the driving member, the other end of the connecting block is connected with the first connecting rod and the second connecting rod, one end of the first connecting rod is rotatably connected with the connecting block, the other end of the first connecting rod is rotatably connected with the first injector, one end of the second connecting rod is rotatably connected with the connecting block, and the other end of the second connecting rod is rotatably connected with the first injector; and the working portion comprises a frame body, a first bracket and a second bracket, the first injector is connected with the first bracket, the first bracket is provided with a first outlet hole, the needle of the first injector is capable of extending out of the working portion relative to the first outlet hole, the second bracket is provided with a second outlet hole, and the needle of the second injector is capable of extending out of the working portion relative to the second outlet hole.

* * * * *